US00PP29398P2

(12) United States Plant Patent
Bédard

(10) Patent No.: US PP29,398 P2
(45) Date of Patent: Jun. 19, 2018

(54) FLORIBUNDA ROSE PLANT NAMED 'WEKWIBYSICPEP'

(50) Latin Name: *Rosa hybrida*
Varietal Denomination: WEKwibysicpep

(71) Applicant: Early Morning LLC, Lawrenceburg, IN (US)

(72) Inventor: Christian Bédard, Placentia, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days. days.

(21) Appl. No.: 15/530,016

(22) Filed: Nov. 18, 2016

(51) Int. Cl.
*A01H 5/02* (2018.01)

(52) U.S. Cl.
USPC ..... Plt./141
CPC ..... *A01H 5/0222* (2013.01)

(58) Field of Classification Search
USPC ..... Plt./141, 149, 148
CPC ..... A01H 5/0222
See application file for complete search history.

(56) References Cited

U.S. PATENT DOCUMENTS

PP11,562 P 10/2000 Zary

OTHER PUBLICATIONS http://forums2.gardenweb.com/discussions/3601518/violets-pride-70-bushes-in-bloom; Jan. 8, 2016; 9 pages.*
Weeks Roses, 2017 Catalog, 92 pages.

* cited by examiner

*Primary Examiner* — Kent L Bell
(74) *Attorney, Agent, or Firm* — McKee, Voorhees & Sease, PLC

(57) ABSTRACT

A new variety of Floribunda rose suitable for garden decoration, having flowers of lavender with a magenta heart coloration.

1 Drawing Sheet

Classification: The present invention relates to a new *Rosa hybrida* plant.

Variety denomination: The new plant has the varietal denomination 'WEKwibysicpep'.

BACKGROUND OF THE INVENTION

This invention relates to a new and distinct variety of Floribunda Rose. It has a non-disseminated seedling of my creation as its seed parent with the following genetic origin {[(International Herald Tribune×*Rosa soulieana* derivative)×(Sweet Chariot×Blue Nile)]×[Blueberry Hill×Stephen's Big Purple]} and a non-disseminated seedling of my creation as its pollen parent with the following genetic origin (Crystalline×Perfume Perfection).

SUMMARY OF THE INVENTION

Among the features which distinguish the new variety from other presently available and commercial rose cultivars known to the inventor are the following combinations of characteristics: its high degree of resistance to powdery mildew, downy mildew and rust, its strong grapefruit and fruity fragrance with hints of spices and its unique lavender with a magenta heart flower coloration. The plant has a rounded bushy moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKwibysicpep' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKwibysicpep' bears very double flowers (about 29 to 65 petals) of lavender with a magenta heart coloration, the non-disseminated seedling bears double flowers of red-purple with a lavender eye coloration with significantly lesser petalage (about 25 to 38 petals). The new variety has a strong grapefruit and fruity fragrance with hints of spices, whereas the seed parent has a slight fruity fragrance.

The new variety may be distinguished from its pollen parent, a non-disseminated seedling of my creation by the following combination of characteristics: whereas 'WEKwibysicpep' bears very double flowers (about 29 to 65 petals) of lavender with a magenta heart coloration, the non-disseminated seedling bears double flowers of lavender coloration with significantly lesser petalage (about 22 to 32 petals). The new variety has a rounded bushy moderately spreading medium height growing habit (about 120 to about 160 cm. in height), whereas the pollen parent has an upright significantly taller growing habit (about 160 to about 180 cm. in height).

COMPARISON WITH THE CLOSEST COMMERCIALLY AVAILABLE CULTIVAR

The new variety may be distinguished from its closest commercially available cultivar, 'JACshok' (U.S. Plant Pat.

No. 11,562) by the following combination of characteristics: whereas 'WEKwibysicpep' bears very double flowers (about 29 to 65 petals) of lavender with a magenta heart coloration, 'JACshok' bears double flowers of lavender-pink coloration with significantly lesser petalage (about 25 to 30 petals). The new variety has a strong grapefruit and fruity fragrance with hints of spices, whereas the closest commercially available cultivar has a strong lemon fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, sometimes in clusters of two to five or more per stem. Flowers may be borne in regular rounded clusters on strong somewhat short to medium length stems (about 20 to about 52 cm.). The cluster ranges from about 11.2 to about 22.0 cm. in diameter. Outdoors, the plant blooms abundantly and nearly continuously during the growing season. The flowers have a strong grapefruit and fruity fragrance with hints of spices.

BUD

The peduncle is about 2.1 to about 5.5 cm. in length, of average to somewhat heavy caliper (about 0.2 to about 0.3 cm. in diameter), and usually erect. It is moderately rough, with some stipitate glands and some hairs. Peduncle color is between 146B and 146A.

Before the calyx breaks, the bud is about 1.0 to about 1.6 cm. in diameter at the widest point, about 1.1 to about 1.7 cm. in length, and moderately ovoid to somewhat pointed in shape. The surface of the bud bears between 5 to 10 foliaceous appendages with some stipitate glands and few hairs, usually with slender entire foliaceous parts extending beyond the tip of the bud about ½ or more of its length. Bud color is between 138A and 146A.

The sepals are 5 per flower, about 2.1 to about 2.8 cm. in length and about 0.8 to about 1.1 cm. in width at the widest point. The outer surface color of the sepal is between 138A and 146A. The outer surface of the sepal is somewhat rough and bears between 0 to 4 foliaceous appendages with some stipitate glands and few hairs. The inner surface color of the sepal is near 146C broadly bordered by near 137B. After the sepals open, the inner surface color is sometimes lightly suffused, especially on the area exposed to the sun, with between 187B and 187C. The inner surface of the sepal is covered with fine wooly tomentum; sepal margins are entire and lined with some stipitate glands and hairs. The sepals are moderately fugacious, usually straight in shape with acute apices.

The receptacle of the flower is of somewhat short to medium length (about 0.5 to about 0.8 cm.) and moderately thin to average in caliper (about 0.7 to about 1.1 cm. in diameter). The receptacle is cup-shaped in form. Its surface is smooth with few hairs and with somewhat thin fleshy walls. The receptacle color is between 146B and 146A.

As the petals open (after the calyx breaks), the bud is about 1.7 to about 2.2 cm. in diameter at the widest point, about 1.6 to about 2.2 cm. in length, and moderately ovoid to somewhat pointed in form. The color of the under and upper surfaces of the newly opened petals is between 75B and 65D often moderately suffused with between 64B and 61B. At the point where the petal attaches, there is a large zone of between 145D and 149D.

BLOOM

When fully open, the bloom ranges from about 6.7 to about 9.2 cm. in diameter. Petalage is very double with about 29 to 65 petals and about 5 to 9 petaloids irregularly arranged. When partially open, the bloom form is moderately globular to somewhat cupped, and the petals are tightly spiraled to cupped with petal edges somewhat reflexed outward. When fully open, the bloom form is more cupped, and the petals are loosely cupped to somewhat undulated with petal edges somewhat reflexed outward.

PETALS

The substance of the petals is somewhat heavy and of moderately thin to medium thickness, with upper surfaces moderately satiny and under surfaces slightly shiny. The petals are about 3.0 to about 5.2 cm. in length and about 2.5 to about 5.7 cm. in width at the widest point. Petal margins are entire.

The outer petals are somewhat obovate in shape with rounded apices.

The inner petals are broadly obovate in shape with rounded apices.

Petaloids are about 1.1 to about 3.8 cm. in length and about 0.3 to about 2.2 cm. in width at the widest point. Petaloids are irregularly shaped somewhat oblanceolate with rounded apices.

NEWLY OPENED FLOWER

The under and upper surface color of the outer petals is between 75D and 69B sometimes lightly suffused with between 74B and 70B. At the point where the petal attaches, there is a large zone of between 155A and 155C.

The under surface color of the intermediate and inner petals is between 75D and 69B often lightly suffused with between 74B and 70B. The upper surface color of the intermediate and inner petals is between 75D and 69B often moderately suffused with between 74B and 70B.

The under and upper surface colors of the petaloids are similar in coloration to the upper and under surfaces of the intermediate and inner petals.

The general tonality of the newly opened flower is between 75D and 69B often moderately suffused with between 74B and 70B.

THREE-DAY-OLD FLOWER

The under and upper surface color of the outer petals is between 84D and 69C sometimes lightly suffused with between 78A and 78B. At the point where the petal attaches, there is a large zone of between 155A and 155C.

The under surface color of the intermediate and inner petals is between 84D and 69C sometimes lightly suffused with between 78A and 78B. The upper surface color of the intermediate and inner petals is between 84D and 69C often moderately suffused with between 78A and 78B.

The under and upper surface colors of the petaloids are similar in coloration to the upper and under surfaces of the intermediate and inner petals.

The general tonality of the three-day-old flower is between 84D and 69C often moderately suffused with between 78A and 78B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 90) and are arranged regularly about the pistils; a few are mixed with petaloids. The filaments are of somewhat short length (about 0.3 to about 0.7 cm.) most with anthers. Filaments are between 3C and 4B in color. The anthers are medium to somewhat large for the class and all open approximately at the same time. Anther color when immature is near 22A on the external part and near 11D on the internal part. Anther color at maturity is near 165B on the external part and near 200A on the internal part. Pollen is moderate and between 22B and 23C in color.

FEMALE REPRODUCTIVE ORGANS

Pistils vary in number (average about 50). The styles are moderately even, somewhat long in length (about 0.4 to about 0.8 cm.), moderately thin in caliper, and loosely bunched to somewhat separated. Stigma color is between 18C and 19C. Style color is between 154C and 150C usually heavily suffused with between 60A and 59B. Ovaries are usually all enclosed in the calyx. The ovaries are of small size and between 158B and 158C in color.

Hips have not been observed on this variety when grown in Pomona, Calif.

FOLIAGE

The compound leaves are usually comprised of three to nine leaflets and are borne abundantly. The seven-leaflet leaves are about 10.0 to about 14.0 cm. in length and about 7.3 to about 9.9 cm. in width at the widest point, moderately leathery to somewhat crisp in texture on both sides, and glossy in finish on the upper side and semi-glossy in finish on the under side. The leaves have a pinnate venation pattern. The terminal leaflets are about 4.0 to about 5.7 cm. in length and about 2.3 to about 3.7 cm. in width at the widest point, shaped oval to somewhat ovate with acute to somewhat acuminate apices and rounded bases. Their margins are usually simply serrate.

The upper surface color of the mature leaf is between 137A and 147A. The under surface color of the mature leaf is between 137C and 146A. The under and upper colors of the leaf veins on the mature leaf are similar in coloration to the upper and under surfaces colors of the mature leaf. The upper surface color of the young leaf is between 137C and 146A, often lightly suffused with between 187B and 187A. The under surface color of the young leaf is between 146B and 146A, often lightly suffused with between 187B and 187A. The under and upper colors of the leaf veins on the young leaf are similar in coloration to the upper and under surfaces colors of the young leaf.

The rachis is about 6.0 to about 8.3 cm. in length, about 0.1 to about 0.2 cm in width at the widest point and rough. The upper side is deeply grooved with some hairs and few stipitate glands on the edges of the grooves. The under side of the rachis is rough with few stipitate glands and small prickles. The rachis color is near 146D on the under side and near 137C on the upper side, often lightly suffused on the young leaves with between 187B and 187A.

The stipules are about 0.9 to about 1.4 cm. in length and moderately wide (about 0.6 to about 0.9 cm.) with long straight points that usually turn out at an angle of more than 45 degrees. The under and upper surface color of the stipule is between 137B and 137C. The upper and under surfaces of the stipules are smooth in texture.

The petiole is somewhat light to average in caliper and rough. The upper side is deeply grooved with some hairs and few stipitate glands on the edges of the grooves. The under side of the petiole is rough with few stipitate glands and small prickles. The petiole is about 0.3 to about 1.1 cm. in length and about 0.1 to about 0.2 cm in width at the widest point. The petiole color is near 146D on the under side and near 137C on the upper side, often lightly suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has a rounded bushy moderately spreading medium height growing habit (about 120 to about 160 cm. in height and about 120 to about 170 cm. in diameter at the widest point), with full branching. It displays moderately vigorous growth and the canes are of medium to somewhat heavy caliper for the class (about 1.3 to about 2.8 cm. in diameter at the widest point).

The color of the major stems is between 146A and 146B. The major stems are rough in texture and they bear some large prickles that are about 0.6 to about 0.9 cm. in length. The large prickles are hooked slightly downward with a medium length somewhat narrow oval base; prickle color is between 199A and 199B often moderately suffused with between 201B and 201C. The major stem bears few small prickles of similar shape and coloration. The color of the branches is between 146B and 146A. The branches are rough in texture and they bear some large prickles which are of similar size and shape to the large prickles on the major stems; prickle color is between 164A and 165B. The branches bear few small prickles of similar shape and coloration. The color of the new shoots is between 146B and 146A sometimes lightly suffused with between 187B and 187A. The new shoots are rough in texture and they bear some large prickles which are of similar size and shape to the large prickles on the major stems; prickle color is between 147B and 148B often moderately suffused with between 187B and 187C. The shoots bear few small prickles of similar shape and coloration.

I claim:

1. A new and distinct Floribunda rose plant of the variety substantially as described and illustrated herein.

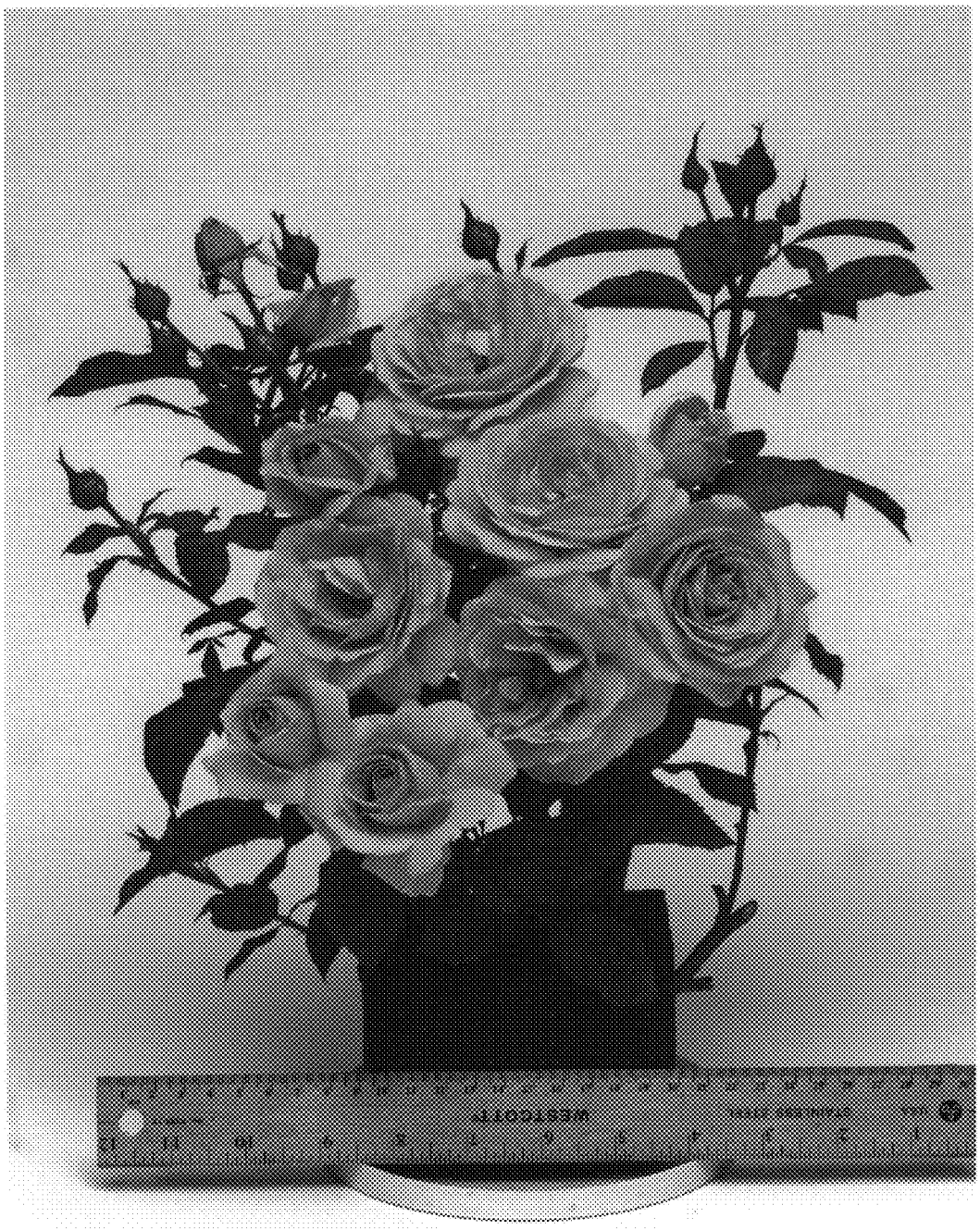

* * * * *